United States Patent
Prest (12)

(10) Patent No.: US 6,484,560 B1
(45) Date of Patent: Nov. 26, 2002

(54) IN SITU CONCENTRATION OF AN ANALYTE

(75) Inventor: Harry F. Prest, Santa Clara, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/708,794

(22) Filed: Nov. 7, 2000

(51) Int. Cl.7 .............................. G01N 1/00; B01L 3/02
(52) U.S. Cl. ................. 73/23.41; 73/23.42; 73/864.81; 73/864.21; 95/86; 96/105
(58) Field of Search .................. 73/23.35, 23.39, 73/23.41, 23.42, 864.21, 864.87; 95/86; 96/105

(56) References Cited

U.S. PATENT DOCUMENTS

| | | | |
|---|---|---|---|
| 4,786,475 A | * 11/1988 | Trestianu et al. | 422/54 |
| 4,972,729 A | * 11/1990 | Schomburg et al. | 73/863.11 |
| 5,252,109 A | * 10/1993 | Munari et al. | 95/87 |
| 5,347,844 A | * 9/1994 | Grob et al. | 73/23.41 |
| 5,412,208 A | 5/1995 | Covey | 250/288 |
| 5,472,670 A | * 12/1995 | Harrington et al. | 250/425 |
| 5,508,204 A | * 4/1996 | Norman | 210/198.2 |
| 5,711,786 A | * 1/1998 | Hinshaw | 73/23.25 |
| 5,762,877 A | * 6/1998 | Brewer | 210/198.3 |
| 5,847,291 A | * 12/1998 | Green et al. | 73/863.33 |
| 5,929,321 A | * 7/1999 | Bertrand | 73/23.35 |
| 5,944,877 A | 8/1999 | O'Neil | 96/101 |
| 5,945,678 A | 8/1999 | Yanagisawa | 250/423 |
| 6,062,065 A | * 5/2000 | Sugimoto et al. | 73/23.35 |
| 6,093,371 A | * 7/2000 | Wilson | 422/89 |
| 6,180,060 B1 | * 1/2001 | Green et al. | 366/108 |
| 6,190,613 B1 | * 2/2001 | Watanabe et al. | 422/101 |

* cited by examiner

*Primary Examiner*—Hezron Williams
*Assistant Examiner*—Michael Cygan
(74) *Attorney, Agent, or Firm*—Timothy H. Joyce

(57) ABSTRACT

An apparatus and method for selectively concentrating an analyte on an apparatus by evaporating solvent from the analyte. Concentration is performed by heating or by flowing a gas stream over the analyte to evaporate solvent from the analyte. The invention also provides a method to be used in conjunction with the apparatus.

24 Claims, 4 Drawing Sheets

IN SITU CONCENTRATION OF AN ANALYTE

TECHNICAL FIELD

The present invention relates to the field of chromatography and more particularly toward an apparatus and method for concentrating an analyte prior to an analytical detector such as a mass spectrometer.

BACKGROUND

Although analytical instrumentation is becoming increasingly sensitive and analyte detection continues to improve, many chemical analytes require concentration prior to chemical analysis. Typically this is done using bench-top chemical processes specifically developed or tailored to the analytical problem. Representative of these approaches are solvent condensation or evaporation techniques that eliminate the solvent while retaining the analyte (or analytes—in all cases analyte could just as well as be analytes) by exploiting differences in physical properties such as volatility. Nitrogen or inert gas "blown-downs", rotary evaporation, Kuderna-Danish condensers, distillation (steam, etc.), tube heaters, vacuum evaporation, (freeze drying), and related techniques are typical of approaches to pre-concentrate an analyte by removal of a solvent. A number of commercial machines exist specifically for this purpose such as RapidVap™, CentriVap™, SafetyVap™, as examples. Physical techniques such as centrifugation or selective adsorption (solid-phase extraction, column chromatography), selectively separate analytes from a bulk phase prior to redesolving in another solvent prior to injection. It is after these bench-chemistry steps that an analyte has been concentrated to an appropriate degree that makes detection and quantitation possible with an existing detector. These steps are time-consuming, subject to loss, usually require specialized equipment and technical expertise all of which lead to increased expense.

In gas chromatography, large volume injection techniques have been developed with special hardware (pre-column inlets) to allow more sensitive detection by evaporation of solvent while attempting to retain analyte inside the pre-column inlets prior to the analyte being delivered to the analytical column for chromatographic separation and analysis/detection. Typical volumes are less than or equal to 100-$\mu l$ (by single injection) and the most frequent approach is to inject the solution, either in portion or in entirety, then evaporate the solvent, which is vented from the chromatograph, and transfer the analyte to the analytical column. This approach suffers from a limitation on volume that can be contained inside the pre-column inlet and, therefore, any increases in volume must be obtained by consecutive injections and evaporation cycles that can result in sample losses. These pre-column inlets that thermally program the vaporization of the solvent are called PTVs.

Another similar approach is the cool-on-column solvent venting arrangements that use a long, large diameter of capillary tubing (approximately 1 ml volume) to retain the injected volume. The operation is again the same as the PTV in that the temperature is programmed to vaporize the solvent and retain the analyte. Again the injection volume is fixed by the mechanical configuration of the assorted tubing. In both these approaches the ability to retain analytes is determined by the difference in the boiling point between the solvent and the analyte and the ability of the pre-column inlet and /or analytical column (phase) to selectively capture and retain the analyte.

However, these large-volume pre-column inlets have been considered attractive relative to the standard pre-column inlet such as split/splitless or on-column that only allow less than 4-$\mu l$ injections and provide no capability for in-situ concentration.

Both the standard volume pre-column inlet arrangements and the existing large volume port technologies are limited in the volume that can be concentrated by the fact that liquid injections vaporize inside the port and mechanical arrangements (namely, the liquid or vapor volume that can be contained) place an upper bound on the concentration factors that can be achieved. It would be desirable to obtain in-situ concentration that is flexible and less constrained in the concentration factors that can be obtained.

In the biochemical and organic chemistry fields there is often a need to concentrate an analyte before it is loaded into an analytical instrument. For instance, some products may need to be concentrated, because they are expensive to derivatize, difficult to extract or synthesize. Small amounts of product or intermediates are produced and need to be characterized and identified accurately before proceeding to future research steps. However, low concentrations of product can be a problem for a researcher, because they may challenge the limits of instrument sensitivities or increase the possibility of inaccurate abundance measurements. In addition, the transfer of these analytes from instrument to instrument or from instrument to storage container can result in significant additional loss of product. For these reasons, simple techniques and instruments for both concentrating and analyzing analytes would be of interest to researchers.

A number of instruments already exist for concentrating analytes. For instance, in the biochemical fields analytes may be concentrated using centrifuges, ultra-centrifuges and filtering. A number of commercial products exist for this purpose. For instance, Amicon™ produces a number of filters that allow for desalting of samples, removal of solvent and concentration of small amounts of analyte. However, these devices often require access to a centrifuge or micro-centrifuge for spinning the analytes and are effective only when concentrating small volumes.

On a larger scale, typical analyte concentration is performed on the bench top using rotary evaporation, K-D, dry nitrogen blow down or in a PTV injection port by depositing the analyte in a liner and then evaporating the solvent by heating the liner. Each of these methods provides for concentration of analyte by removal of solvent. However, most of these methods and instruments suffer from the limitation of possible loss of analyte. In addition, since the concentration of analyte is performed separately, these methods can be time intensive and laborious. It would, therefore, be of particular interest to be able to concentrate an analyte without having to transfer, or resolvate the analyte.

Recent trends in analytical instrumentation include components for concentrating analytes in situ (i.e. directly in the instrument or more preferably before the analytes are introduced onto the pre-column). For instance, quartenary pumps are being used in HPLC instruments to pre-mix analytes before the analyte is injected and separated. Present chromatographic technology, however, requires additional hardware, components or complex instrumentation design to appropriately concentrate analytes. In addition, most of the chromatography instrumentation is designed to concentrate the analyte inside the pre-column just before it is introduced onto the column. A problem with this type of device is that the analyte is too dilute or contains a volatile solvent that significantly lowers the amount of sample concentration. It would, therefore, be desirable to be able to adapt existing chromatography hardware to serve the purpose of concentrating analytes in situ (i.e. on the syringe needle tip). A brief review of pre-column inlets, therefore, is in order to clarify existing technology that may be adapted to serve these purposes.

A number of different pre-column inlets or injectors exist to provide accurate, reproducible and predictable introduction of analytes into gas chromatography columns. Usually the analyte is a liquid and can be injected using a syringe, but other devices are available. For instance, analytes can be introduced onto columns by automatic analyzers or valves. Pre-column inlets can be divided into two major categories including packed-column inlets and capillary-column inlets. In gas chromatography the packed column inlets are fairly popular. A second type of column called a capillary-column inlet is also quite popular. These inlets include: capillary direct or (vaporizing inlet), split/splitless inlets (a vaporizing inlet), programmed temperature vaporizer inlets (vaporizing) and cool-on-column (non-vaporizing) inlets.

Capillary inlets are used with wide-bore capillary columns (I.D.≧0.5 mm) and are made by substituting a special insert inside a packed-column inlet. The two types of inlets, including the split and splitless inlets, are quite different in design and operation. The split inlet was the earlier design and is a vaporizing inlet that vents most of the analyte in the split mode and transfers most of it to the column in the splitless mode. The splitless inlets load the analyte directly onto the column whereas the split inlets allow for loading partial amounts of analyte onto the column while at the same time allows venting of a portion of the final analyte. Programmed temperature vaporizer (PTV) inlets combine the benefits of split, splitless and on-column inlets. Analytes are usually injected into a cool liner and no syringe needle discrimination can occur. Inlet temperature is then usually increased to vaporize the analyte. A variety of user programs can then be used to provide determined vent times and temperatures to achieve results similar to split or spiitless transfers. PTV injection provides the most flexibility. Other advantages of PTV inlets include: the ability to trap non-volatile components in a liner, removal of solvent and low boiling components, use of large injection volumes, no special syringe needed, no syringe needle discrimination, retention time and high reproducibilities similar to cool on column injections. A number of commercial injectors exist for these purposes. For instance, the Apex Prosep™ pre-column inlet is highly versatile and may be used for injecting analytes. The system includes a standard inlet that contains both temperature and vaporizing regulation. However, these systems have only been used to concentrate analytes after they have been ejected from the syringe needle into the pre-column inlet. A number of techniques are used at this point to concentrate, or focus, the injected analtye. The major focusing techniques include stationary phase focusing, solvent focusing and thermal focusing.

Stationary phase focusing is the most frequently used technique and is possible only in temperature-programmed analysis. Generally, in gas chromatography, retention is a function of temperature. For instance, the speed at which the solutes travel down the column is dependent upon the temperature changes. As the temperature is increased, the solutes increase their speed of separation and as the temperature is lowered, they slow their movement. As the vaporizing analyte moves from the inlet to the column, it comes in contact with the stationary phase and is trapped in a defined range. The lower the applied temperature, the more effective the focusing.

Solvent focusing occurs in a different fashion compared to stationary phase focusing. For instance, as a condensed solvent starts to evaporate, solutes with volatility similar to that of the solvent tend to concentrate and focus on the solvent tail. This technique yields very narrow peaks.

Thermal focusing is the last technique and relates to the condensation of gases in a tube or at the head of the column. Peaks narrow as the solute volume is reduced during condensation. This technique is particularly helpful in narrowing bandwidths when the column temperature is approximately 150° C. below the boiling point of the solvent. In addition, thermal focusing does not rely on chromatographic processes. It only requires a surface on which vapors can condense. To date, each of these techniques has been applied to a gas chromatography column or pre-column inlets. These techniques are not designed for concentrating the analyte at the pre-column stage. A disadvantage of this is that lower amounts of analyte are loaded onto the column and by the time the separated components reach the final mass analyzer, a low signal to noise ratio is obtained. This negatively affects the overall results. Therefore, there is a substantial need for an apparatus and method that concentrates the analyte before it is injected into the pre-column inlet.

OBJECTS AND SUMMARY OF THE INVENTION

Accordingly, it is an object of the present invention to overcome the above-mentioned disadvantages of the prior art by providing a novel method and apparatus for selectively removing solvent and concentrating an analyte before it is subject to chromatographic analysis.

It is another object of the invention to provide an improved method and apparatus for concentrating an analyte in situ using an instrument pre-column inlet port and syringe.

It is a still further object of the invention to provide an improved method of removing solvent from an analyte before injection into a pre-column inlet port or chromatographic column.

Additional objects, advantages and novel features of the invention set forth in part in the description which follows, and in part will become apparent to those skilled in the art upon examination of the following, or may be learned by the practice of the invention.

In a general aspect, then, the present invention relates to an apparatus for concentrating an analyte at a gas chromatograph (GC). The apparatus has a dispensing means for holding and dispensing an analyte, an injection means for receiving the dispensing means, and a concentration means in contact with the injection means for concentrating the analyte on the dispensing means. The dispensing means may include an auto-sampler having a syringe with a needle and tip or similar type device. The dispensing means may also comprise the syringe needle and tip without the auto-sampler. The injection means includes a pre-column inlet having an inlet port designed for receiving the dispensing means. The concentration means is in contact with the injection means and is designed for evaporating or heating and removing the solvent from the analyte at the dispensing means. The concentration means may be a heater or a gas inlet port.

The invention also includes a method of removing solvent from an analyte and concentrating the analyte in a mass spectrometer. The technique accomplishes the concentration before the analyte is injected into a pre-column inlet and loaded onto a gas chromatograph by first collecting the analyte in the dispensing means. The dispensing means is then inserted into the injection means and the solvent is removed from the analyte through evaporation. The evaporation may occur by heating the analyte or by applying a gas stream. The concentrating means uses a combination of solvent and/or thermal focusing to concentrate the analyte.

Additional objects, advantages and novel features of the invention will be set forth in the part in the description which follows, and in part will become apparent to those skilled in the art upon examination of the following, or may be learned by practice of the invention.

BRIEF DESCRIPTION OF THE FIGURES

The invention is described in detail below with reference to the following figures.

DETAILED DESCRIPTION OF THE INVENTION

Overview and Definitions

Figure 1:
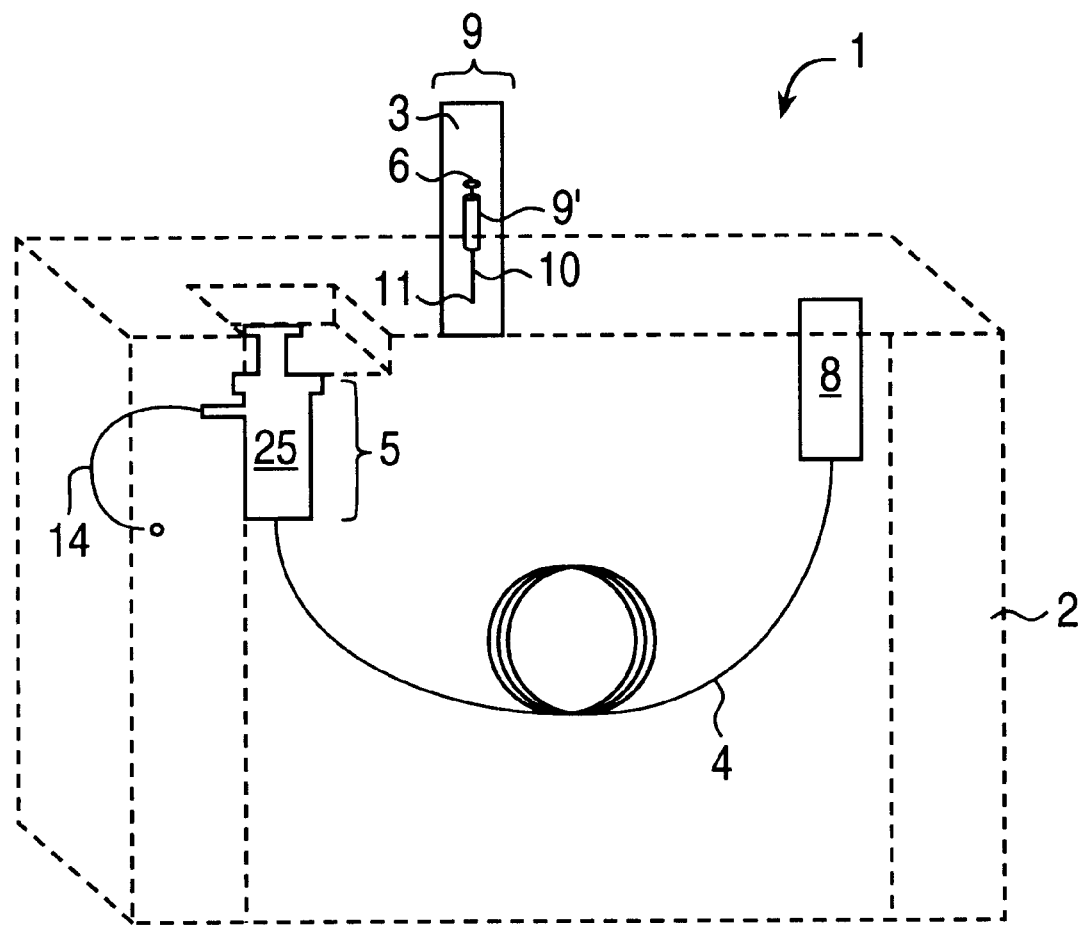
FIG. 1 is a perspective view of a chromatograph showing a first embodiment of the present invention.

Before describing the present invention in detail, it is to be understood that this invention is not to be limited to specific compositions, gases, process steps, or equipment, as such may vary. It is also to be understood that the terminology used herein is for the purpose of describing particular embodiments only, and is not intended to be limiting.

It must be noted that, as used in this specification and the appended claims, the singular forms "a", "an", and "the" include plural referents unless the context clearly dictates otherwise. Thus, for example, reference to "an inlet", includes more than one inlet, reference to "a needle" includes more than one needle and the like.

In describing and claiming the present invention, the following terminology will be used in accordance with the definitions set forth below.

The term "in situ" shall refer to an analyte that is concentrated before addition to a gas chromatography pre-column. Pre-columns have inlets, inlet ports and other similar types of devices and valves for receiving analytes.

The term "auto-sampler" should be construed broadly to include any device that can deliver a defined or graduated amount of sample or solvent to a specific location over time. The device may be manual, machine or computer operated. In addition, the device may contain a manual feedback loop or data processing control system for operation of the device for sample delivery.

The term "pre-column", "pre-column inlet" or "inlet" shall refer to any device that is attached to the beginning of a column and is used for preparing the analyte for introduction onto the column. Various pre-columns are used to filter and remove contaminants from the analyte before it has been added to the column. The term should be construed broadly to include both mass spectrometer technology and other analytical instruments that require sample concentration before analysis.

The term "syringe" shall refer to any device, apparatus or instrument used for introducing or dispensing an analyte volume into a chromatograph pre-column inlet port.

The term "needle" shall refer to the exterior end or elongated shaft of a syringe that is used for inserting and injecting a sample into a pre-column inlet port.

The term "port" or "pre-column inlet port" shall refer to any zone or aperture of a pre-column designed for receiving a syringe needle, syringe needle tip or the like.

The term "time-delayed delivery" shall refer to the delayed delivery of an analyte to a pre-column inlet port. In particular, it shall refer to the delay in time when the syringe needle is inserted into an inlet port and paused before removal and sample dispensing. This allows the syringe needle tip to sit idle in a defined position for a period of time so that solvent can be removed from the analyte. Solvent removal is accomplished by exposing the syringe needle tip and analyte to a high temperature or flowing gas.

The invention is described herein with reference to the figures, in which like parts are referenced by like numerals. The figures are not to scale and in particular, certain dimensions may be exaggerated for clarity of presentation.

Theory of function

The mechanism of concentration is the preferential evaporation of the solvent relative to the analyte. This requires some difference in boiling points between the solvent and any analyte(s) dissolved in the solvent. This can be described by a difference in boiling points and volatilities as well as other physical chemical constants that reflect these parameters such as the Henry's Law constant. At the surface of the liquid solution at the needle tip, solvent must evaporate more readily than the analyte(s). This can be manipulated to a certain degree by the temperature as indicated by the Clausius-Clapeyron equation that describes the variation of vapor pressure with temperature:

$$P_a = P_b(\exp-\{(\Delta Hvap/R)(T_a^{-1} - T_b^{-1})\}),$$

where $P_i$ is the vapor pressure of a liquid at temperature $T_i$; R is the universal gas constant; and $\Delta Hvap$ is the enthalpy of vaporization. Trouton's rule suggests that most liquids, i.e., typical solvents, have approximately the same entropy of vaporization and therefore:

$$\Delta Hvap = T_{bp}(85J\ K^{-1}mol^{-1})$$

where $T_{bp}$ is the boiling point of the liquid.

Typically the solvent is much more volatile than the analyte in GC/MS analysis and so the relative evaporation is not an issue; i.e., the analytes are typically solids or viscous liquids with no appreciable vapor pressure under the conditions of operation. However, the equations show that as long as the vapor pressure of the analyte is lower than the solvent there will be concentration of the analyte.

Further, as the solvent evaporates there will be a tendency for the temperature of the remaining solvent to cool due to the heat required for evaporation by virtue of the finite heat of vaporization. This cooling will reduce the vapor pressure of solvent and analyte, but because the solvent is available in excess this will further favor retention of the analyte.

As the pressure on a liquid increases, the vapor pressure increases, therefore, the size and shape of the orifice from which the controlled delivery of the solvent will take place can be modified to maximize the surface area and its curvature. Higher curvature implies higher pressure and, therefore, higher vapor pressure by the Kelvin equation. A needle with a single opening will produce a droplet with relatively high surface area and curvature with a high rate of evaporation. An array of small orifices will greatly increase the area available for evaporation and, therefore, the rate of evaporation.

Referring to the figures, FIG. 1 shows a perspective view of a chromatograph 1. The chromatograph 1 comprises a dispensing means 9, an injection means 5, and a concentration means 25 (the concentration means 25 is labeled and shown in FIG. 1). The dispensing means 9 may be disposed anywhere on chromatograph housing 2. The injection means 5 is generally disposed within the chromatograph housing 2 close enough to the dispensing means 9 to receive an analyte 12 (not shown in FIG. 1) delivered by the dispensing means 9. The concentration means is disposed in the injection means 5 and may also be part of the injection means 5. The dispensing means 9 is disposed within or affixed to the mass spectrometer housing 2 and may comprise an auto-sampler 3 designed for preparing the analyte 12 for delivery and separation on a gas chromatography column 4. Auto-sampler 3 may be any manual or automatic delivery system capable of administering defined amounts of analyte 12 at a desired flow rate to the concentration means 25. The gas chromatography column 4 is used for chemical separation of the analyte 12 before it reaches a detector 8.

Figure 2A:
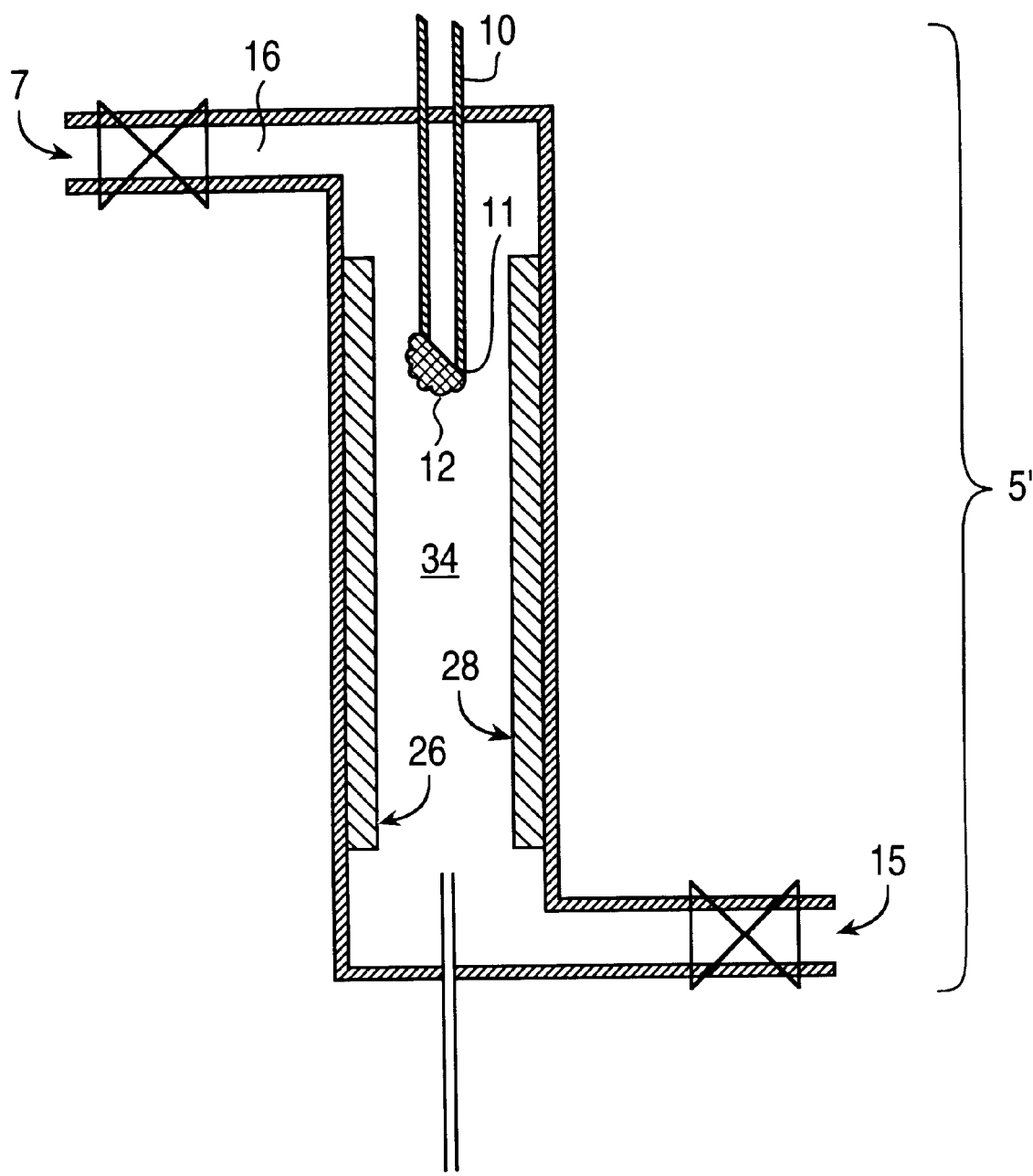
FIG. 2A is a sectional view of a pre-column inlet showing a first embodiment of the present invention.
Figure 2B:
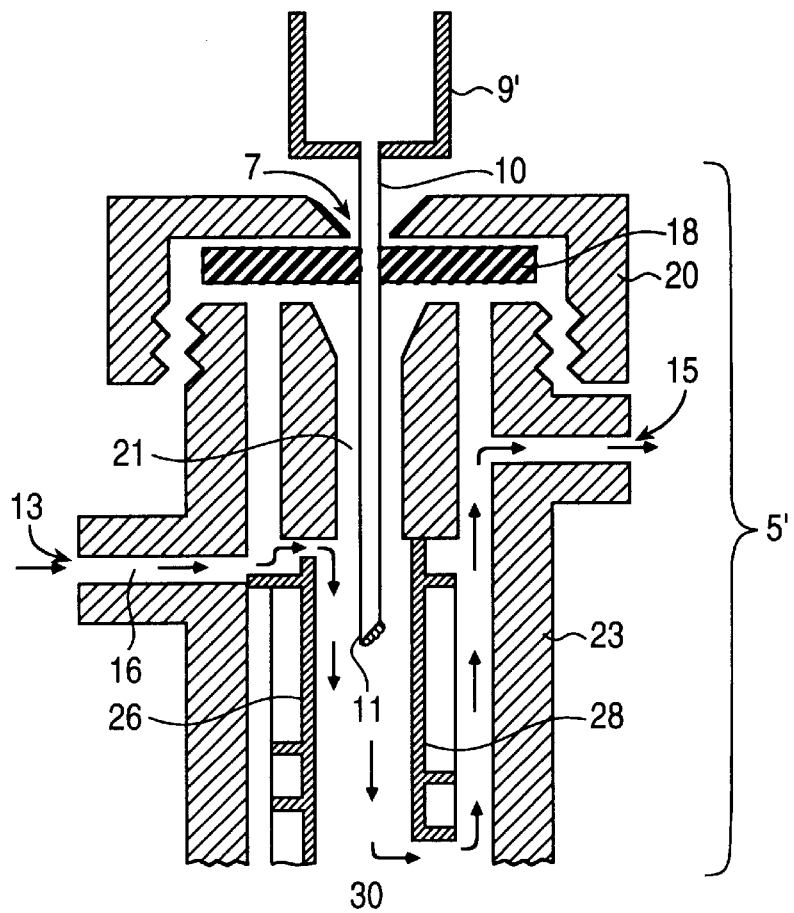
FIG. 2B is a sectional view of a pre-column inlet showing a second embodiment the invention.

FIGS. 2A and 2B illustrate various embodiments of the invention. In particular, they show that an inlet port 7 and gas outlet 15 may be located in various positions on the pre-column inlet 5'.

Referring to FIG. 2A, a first embodiment of the invention, the dispensing means 9 (not shown in FIG. 2A) delivers solvent and dissolved analyte 12 to the syringe needle 10 where evaporation takes place. The needle temperature can be regulated. The temperature of the needle can be regulated by an internal or external heating and/or cooling apparatus that may include a sensor and feedback loop. Internal heater or heating devices should be designed and configured to cause evaporation of solvent from a syringe needle tip 11. In addition, with the feedback loop, the apparatus would be capable of being regulated to a defined temperature. In addition, such a device would be designed for rapid temperature changes for evaporation and cooling of various solvents. In essence the needle and system should be capable of regulated evaporation of solvents having both high and low volatility.

After the analyte 12 with excess solvent is delivered to the syringe needle tip 11, gas (carrier gas) flows over the syringe needle 10 to carry away evaporating solvent that exits the pre-column inlet 5'. The temperature of this gas is also controlled along with the pressure in the pre-column inlet 5'. It is also possible to valve shut the carrier or evaporating gas and apply a vacuum at the lower section of the pre-column inlet 5' near the gas outlet 15 which will allow the solvent to evaporate and exit. Controlling the needle temperature will prevent super cooling and freezing of the solvent at the syringe needle tip 11.

Controlling the temperature of the inlet chamber 34 will prevent re-condensation of solvent and promote condensation of any analyte 12 on the first wall 26 and second wall 28. Coating the first wall 26 and second wall 28 with phase (such as a column phase) will increase retentiveness and selectivity.

Delivery speed is controlled to optimize the retention of analyte 12 versus solvent. Because the variables of temperature, gas flow over the immerging solvent and needle or orifice design can be manipulated, there are several degrees of freedom available to optimize the concentration. Solvent can be evaporated to the point where the solution is nearly saturated—just prior to any precipitation or solid formation. At this point the remainder is rapidly dispensed and delivered into the inlet chamber 34 which can be ramped in temperature to aid delivery to the analytical column or pre-column inlet 5'. Similarly the needle temperature can be ramped simultaneously to enhance removal of analyte 12 and reduce carryover. It should also be mentioned that this method or process may include a compositing injection. In other words, the system can be designed to inject a number of samples or operate in a sequential manner with injections. This could provide for added concentration of analyte in the actual pre-column inlet chamber.

Very high concentration factors are possible in this arrangement if very large differences exist in solvent and analyte volatility. This can be further extended by addition of a "keeper"—a liquid of higher boiling point than the solvent. As an example, addition of toluene to pentane or dichloromethane. The common solvents pentane and dichloromethane boil at 36° C. and 39° C., respectively, while toluene boils at 110° C. Adding a small percentage of toluene will enhance capture of the analytes as the pentane or dicbloromethane evaporate leaving primarily the toluene. For example, adding 10-$\mu$l of toluene to a 500-$\mu$l sample that is primarily dichloromethane would allow in-situ concentration down to the 10-$\mu$l volume (holding the conditions of the gas temperature, port temperature, gas flow velocity, etc., below the boiling point of toluene). Much higher boiling solvents can also be used such as tetradecane, hexadecane, etc. that have even lower volatility than toluene.

FIGS. 1 and 2B show the dispensing means 9 with the auto-sampler 3. The dispensing means 9 may be a syringe 9' having a syringe needle 10 with a syringe needle tip 11 and a syringe plunger 6 (shown only in FIG. 1). The syringe plunger 6 is designed for delivery of the analyte 12 when it is depressed into the main body of a syringe housing 32 (not shown in FIGS. 1 and 2B). The syringe 9' and the syringe needle 10 are also designed to temporarily house the analyte 12 and inject the analyte 12 into the injection means 5 or pre-column inlet 5'. Other types of dispensing means may be utilized with the invention and the invention should not be limited to those disclosed only in the specification. It is a feature of the invention that the dispensing means 9 have the ability to retain the analyte 12 and deliver it to a defined area at a defined rate of speed. In particular, the auto-sampler 3 is designed for depressing the syringe plunger 6 at a steady state or slow rate of speed so that the analyte 12 may be concentrated on the syringe needle tip 11 by the concentration means 25. If the analyte 12 is delivered too fast to the syringe needle tip 11, it may be completely ejected and never concentrated. For these reasons, the auto-sampler 3 and/or the dispensing means 9 or 9' have the capability of exposing the analyte and solvent to a longitudinal bore 21, so that volatile solvents or the like may be removed from the analyte 12 and the analyte 12 concentrated. In addition, the dispensing means 9, the syringe 9' and the auto-sampler 3 must also have the ability to eject the analyte 12 from the syringe needle tip 11 after the analyte 12 has been concentrated to a prescribed level. Knowledge of the rates of solvent evaporation and exposure can be used to regulate relative concentrations that may be desired and the time that the dispensing means 9 or the syringe 9' with syringe needle 10 and the syringe needle tip 11 is fixed in a defined position within the injection means 5 or the pre-column inlet 5'. It is within the scope of the invention that a computer system or feedback loop be connected to the dispensing means 9 or 9' in such a way that the concentration of the analyte 12 can be defined and predicted after the concentration means 25 has been applied to the analyte 12. It is also a feature of the invention that the dispensing means 9, the syringe 9' and the auto-sampler 3 have the ability to delay both delivery of the analyte 12 and removal from the injection means 5 or the pre-column inlet 5'. Without this feature, the concentration means 25 might not have the ability to concentrate the analyte 12 at the syringe needle tip 11. In addition, the dispensing means 9 or the syringe 9' must have the ability to deliver the analyte 12 to the syringe needle tip 11, or similar type of device or component, so that it beads on the syringe needle tip 11 in such a way that the there is maximum surface area of analyte solvent exposed to the concentration means 25. This will allow for removal of excess solvent and concentration of the analyte. For this reason, the dispensing means 9, or the syringe 9' and the auto-sampler 3 must be carefully designed so that enough analyte is exposed at the end of the syringe needle tip 11 without completely ejecting the analyte 12. The syringe needle tip 11 may be designed of a variety of metal and non-metal materials that may promote high capillarity or surface tension at the syringe needle tip 11. The surface and design of the syringe needle tip 11 must also allow for complete removal or ejection of the analyte 12 once the concentration means 25 has concentrated the analyte 12. This time-delayed delivery is known within the auto-sampler art and may be employed in the present invention in a variety of other embodiments that may not be disclosed here.

Referring to FIGS. 1, 2A and 2B, the injection means 5 may comprise the pre-column inlet 5' or similar type of device for receiving the analyte 12. A variety of inlet types exist and may be used with the present invention including and not limited to capillary direct inlets, split and splitless inlets, programmed temperature vaporizer inlets, cool on column inlets and other well known in the art. The programmed temperature vaporizer inlets (PTV) inlets work the best with the present invention, because of the flexibility of the instrument hardware. FIG. 2B shows a cross sectional view of a standard PTV inlet that may be used with the present invention. The pre-column inlet 5' comprises inlet port 7, pre-column housing 23, and gas inlet 13 for receiving a carrier gas and transporting the gas through a gas bore 16, across the longitudinal bore 21, until a gas outlet 15. The gas inlet 13 is connected to a gas supply line 14 that provides the carrier gas (shown in FIG. 1 only). A rubber gasket 18 is mounted near the inlet port 7 and has a centralized bore 19 (not labeled in FIG. 2B) designed for receiving the syringe needle 10. Rubber gasket 18 is secured to pre-column inlet 5' by lug nut 20. The centralized bore 19 is vertically aligned and disposed axially to the longitudinal bore 21, so that the syringe needle 10 may be inserted through the centralized bore 19 and the rubber gasket 18 into the longitudinal bore 21 (the centralized bore 19 is not labeled in any of the FIGS and passes directly through the rubber gasket 18).

After insertion into the longitudinal bore 21, the concentration means 25 may be applied to concentrate the analyte 12. The concentration means 25 may comprise a heater 25' disposed in a first wall 26 and/or a second wall 28, or the gas inlet 13 that receives a carrier gas from a carrier gas line 14 and delivers the gas to a gas bore 16 that begins at the gas inlet 13 and ends at the longitudinal bore 21. The heater may be disposed in any orientation in first wall 26 or second wall 28. In addition, the heater may be an electrical heating system, IR, laser or similar type device. The concentration means 25 concentrates the analyte 12 by means of flowing the carrier gas through the gas inlet 13 or similar type of existing or constructed ports. A combination of thermal and/or solvent focusing may be used. For instance, if both the heater and carrier gas is applied both thermal focusing and solvent focusing will be used to concentrate the analyte and remove unwanted solvent. The invention need not be limited to a single gas inlet and may include a plurality of inlets. However, it is important to the invention that the gas inlet 13 be designed and positioned so that the gas may flow along the syringe needle 10 toward the needle tip 11. This requires that the syringe needle 10 and syringe needle tip 11 be designed to be inserted beyond the gas inlet 13 in the longitudinal bore 21.

Figure 2C:
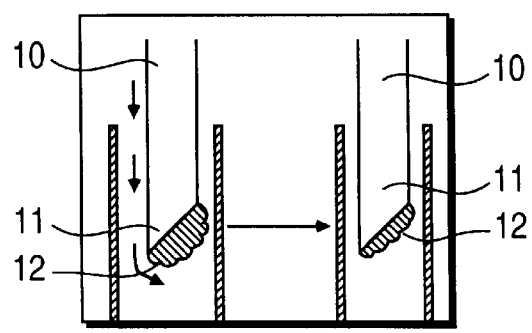
FIG. 2C is an enlarged view of FIG. 2B, showing how the carrier gas or gas stream is applied to the syringe needle tip for removing solvent.

FIG. 2B shows the position of the syringe needle 10 and syringe needle tip 11 in one embodiment of the invention (the injection position). The carrier gas is supplied through the gas inlet 13 and flows down the syringe needle 10 to syringe needle tip 11 and then exits at gas outlet 15. The carrier gas is supplied in a steady and controlled fashion so that solvent may be removed from the analyte 12 that is retained at the end of the syringe needle tip 11. FIG. 2C shows how the gas passes the syringe needle tip 11 and concentrates the analyte 12. Excess solvent is removed by the carrier gas and is carried away through the gas outlet 15, leaving behind the concentrated analyte 12 for final dispensing and delivery onto the gas chromatography column 4. The concentration means 25 provides two functions for the invention. First it allows for the concentration of the analyte 12 directly on the syringe needle tip 11 before the analyte 12 is ejected into the longitudinal bore 21. Secondly, once the analyte 12 has been ejected into the longitudinal bore 21, the concentration means 25 then operates in its known manner and function in the art of concentration the analyte 12 within the walls 26 and 28. In other words, analyte 12 may be subject to concentration both at the syringe needle tip 11 and after it has been injected in the longitudinal bore 21. The analyte 12 is then moved down the pre-column until it reaches the column entrance 30 just before the chromatography column 4.

Figure 3A:
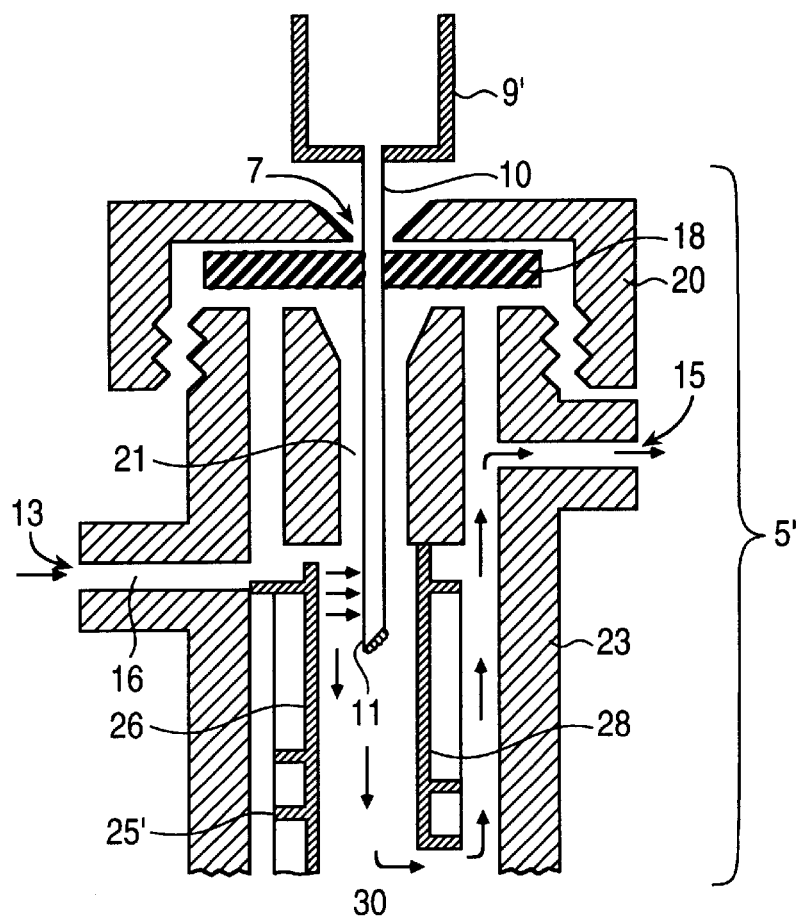
FIG. 3A is a sectional view of a pre-column inlet showing how the solvent can be removed froth the syringe needle tip and analyte by applying a heater.
Figure 3B:
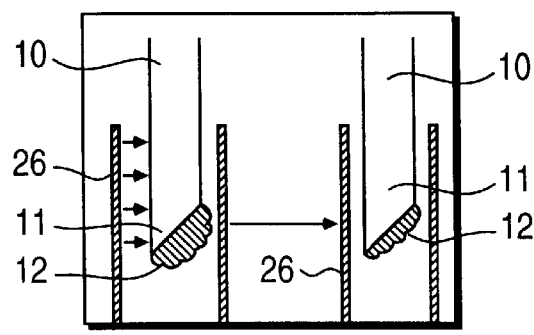
FIG. 3B is an enlarged view of FIG. 3A, showing how the solvent can be removed form the syringe needle tip and analyte by applying a heater.

FIGS. 3A and 3B show a cross-sectional view of a second embodiment of the invention when the syringe needle 10 has been inserted into inlet 5' in its dispensing and concentration position. The first wall 26 and second wall 28 may be designed to contain a heater 25' that may also be used alone or in conjunction with a carrier gas to concentrate the analyte 12. FIG. 3B shows how the analyte would be concentrated, and illustrates an embodiment of the invention where the heater is constructed only in wall 26 of inlet 5'. Excess solvent is removed as shown in FIG. 3B.

Using a port or a zone, it is possible to evaporate or selectively remove solvent just prior to the injection of the analyte 12. As discussed above, the syringe 9' draws-up the analyte 12, moves to the pre-column inlet 5', inserts the syringe needle 10 through the rubber gasket 18, then slowly introduces the analyte 12. A gas (such as a carrier gas) flowing past the needle evaporates the solvent from the syringe needle tip 11. Analytes remain in the solvent at the syringe needle tip 11 rather than being carried away by evaporating the solvent. In addition, this technique has the advantage that the temperature of the gas can be controlled by the speed of the injection or delivery of the solvent to the tip. Coatings can be applied on the syringe needle tip 11, syringe 10, and/or walls 26 and 28 to assist in the recovery of the analyte 12 that tends to escape or evaporate with the solvent. Controlling the temperature of the injection port will allow the collection of analytes over solvent.

EXAMPLE 1

As a specific example, typical analyte concentration factors are around 1000-fold before injecting 1 or 2 micro-liters of solution out of a total volume of 1-ml; i.e., 1000-ml of extraction solvent is condensed to 1-ml. If the injection volume is scaled up to 100 $\mu$l, then to maintain the same effective amount of analyte injected, only a 10-fold concentration factor need be generated on the bench; i.e., 10-ml of extraction solvent is condensed to 1-ml. The extract is concentrated about 20 or 1000 fold. Solvent can be readily removed from analyte according to the results of various tests that may be conducted with the solvent, rate of heating/ gas flow, amount of sample dispensed onto the syringe needle tip, miscibility and volatility of the solvents, shape of the syringe needle tip as well as materials and compositions. Each of these factors could effect the overall final concentration of the analyte that remains on the syringe needle tip. In addition, the rate of gas flow and sample dispensing to the syringe needle tip could be readily determined empirically. Overall concentrations of sample could also be compared to a blank in order to determine initial, transitory and final concentrations of the analyte. Final concentrations will also be dependent upon the rate of delivery of the analyte to the syringe needle tip. Analyte may be delivered and removed in a continuous and/or non-continuous manner from the syringe needle tip.

Now consider that a 1000 micro-liter syringe takes up 1000 micro-liters of analyte and moves into the pre-column inlet for injection. The carrier gas then flows past the needle and the syringe then slowly delivers the analyte to the needle tip where it evaporates and concentrates the analyte. This occurs both on the syringe needle tip and on the port walls. The analyte evaporates from 1000 microliters to only 50 microliters with a 20 fold concentration. This concentrated sample is then further evaporated and concentrated through evaporation from the port walls. There is no benchtop handling and the tip could be multi-channel or multi-tubular for greater speeds of evaporation due to higher surface area. In addition, the evaporating solvent in most cases will cool the syringe or needle tip and locally assist in retaining the more volatile components.

It is to be understood that while the invention has been described in conjunction with the specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

The invention having been thus described, what is claimed as new and desired to secure by Letters Patent is:

I claim:

1. An apparatus for concentration of analyte in a solvent in a gas chromatograph, comprising:
   (a) a dispensing means for holding and dispensing said analyte in said solvent;
   (b) an injection means designed for receiving said dispensing means; and
   (c) a concentration means in contact with said injection means for concentrating said solvent in said analyte on said dispensing means in said gas chromatograph.

2. An apparatus as recited in claim 1, wherein said dispensing means comprises an auto-sampler having a syringe with a syringe needle and syringe needle tip.

3. An apparatus as recited in claim 1, wherein said injection means comprises a pre-column inlet having an inlet port.

4. An apparatus as recited in claim 1, wherein said injection means is on-column.

5. An apparatus as recited in claim 1, further comprising a control system to regulate the flow of said analyte to said dispensing means.

6. An apparatus as recited in claim 1, wherein said concentration means comprises a gas inlet port for dispensing a gas onto said dispensing means and evaporating said solvent from said analyte and concentrating said analyte.

7. An apparatus as recited in claim 6, wherein said gas inlet port is disposed in said pre-column inlet such that when said dispensing means is inserted into said pre-column inlet, a portion of said dispensing means is positioned down stream from said gas inlet port.

8. An apparatus for applying a gas to concentrate an analyte in a solvent in a gas chromatograph, comprising:
   (a) a syringe having a syringe needle and syringe needle tip for concentrating said analyte in said solvent;
   (b) a pre-column inlet having an inlet port for receiving said syringe needle and syringe needle tip; and
   (c) a gas inlet disposed in said pre-column inlet and designed so that when said syringe needle and syringe needle tip are inserted into said pre-column inlet, said syringe needle tip is positioned below said gas inlet wherein said gas causes said analyte solvent to evaporate and concentrate said analyte at said syringe needle tip.

9. An apparatus for concentrating an analyte in a solvent in a gas chromatograph, comprising:
   (a) a syringe with a syringe needle and tip for concentrating said analyte in said solvent;
   (b) a pre-column inlet having an inlet port for receiving said syringe needle and tip; and
   (c) a concentration means disposed in said pre-column inlet for concentrating said analyte in said solvent at said tip of said syringe needle in said gas chromatograph.

10. An apparatus as recited in claim 9, further comprising a control system for controlling the flow of said analyte to said tip.

11. An apparatus as recited in claim 9, wherein said concentration means comprises a gas inlet having an inlet port positioned interior to said pre-column inlet and down stream from said syringe needle wherein said gas pre-column inlet dispenses a gas that evaporates said solvent from said analyte at the tip of said syringe needle tip and concentrates said analyte.

12. An apparatus as recited in claim 9, wherein said concentration means comprises a heater for vaporizing said solvent from said analyte at said syringe needle tip and concentrates said analyte.

13. An apparatus as recited in claim 12, wherein said heater is an electrical heater.

14. An apparatus as recited in claim 12, wherein said heater is an infrared heater.

15. An apparatus as recited in claim 12, wherein said heater is a laser.

16. A method of removing solvent and concentrating an analyte in a chromatograph, comprising the steps of:
   (a) collecting the analyte in a dispensing means;
   (b) inserting the dispensing means into an injecting means;
   (c) applying a concentration means to evaporate said solvent from said analyte to concentrate said analyte on said dispensing means.

17. The method of claim 16, further comprising the step of loading said analyte onto a gas chromatography column.

18. A method of concentrating an analyte in a solvent on a syringe needle tip after insertion into a pre-column inlet, comprising:
   (a) collecting said analyte in said solvent in said syringe needle tip;
   (b) inserting said syringe needle tip into said pre-column inlet;
   (c) applying a stream of gas to said analyte to evaporate said solvent of said analyte and concentrate said analyte on said syringe needle tip.

19. A method of concentrating an analyte in a syringe needle tip as recited in claim 18, wherein said syringe needle tip is inserted into said pre-column inlet and its removal is time delayed.

20. A method of concentrating an analyte in a solvent in a syringe needle tip after insertion into a pre-column inlet, comprising:
   (a) collecting said analyte in said solvent in said syringe needle tip;
   (b) inserting said syringe needle into said pre-column inlet; and
   (c) applying heat to said analyte to evaporate said solvent of said analyte and concentrate said analyte on said syringe needle tip.

21. A method of concentrating an analyte in a solvent on a syringe needle tip after insertion into a a pre-column inlet, comprising:
   (a) inserting said syringe needle tip into said inlet;
   (b) flowing said analyte in solvent onto said syringe needle tip; and
   (c) evaporating said solvent of said analyte to concentrate said analyte on said syringe needle tip.

22. A method as recited in claim 21, wherein steps (a)–(c) are iterative.

23. A method as recited in claim 21, further comprising the step of injecting said concentrated analyte into said pre-column inlet.

24. A method as recited in claim 23, wherein said process is iterative.

* * * * *